United States Patent
DiCianni

(10) Patent No.: US 11,617,863 B2
(45) Date of Patent: Apr. 4, 2023

(54) INTRAVENOUS CATHETER AND GUIDEWIRE ADVANCEMENT MECHANISM

(71) Applicant: Anthony DiCianni, Okemos, MI (US)

(72) Inventor: Anthony DiCianni, Okemos, MI (US)

(73) Assignee: Anthony DiCianni, Okemos, MI (US)

( * ) Notice: Subject to any disclaimer, the term of this patent is extended or adjusted under 35 U.S.C. 154(b) by 108 days.

(21) Appl. No.: 16/916,692

(22) Filed: Jun. 30, 2020

(65) Prior Publication Data
US 2021/0113816 A1    Apr. 22, 2021

Related U.S. Application Data

(60) Provisional application No. 63/034,312, filed on Jun. 3, 2020, provisional application No. 62/947,201, filed on Dec. 12, 2019, provisional application No. 62/937,971, filed on Nov. 20, 2019, provisional application No. 62/936,516, filed on Nov. 17, 2019, provisional application No. 62/923,494, filed on Oct. 19, 2019.

(51) Int. Cl.
*A61M 25/06* (2006.01)
*A61M 25/09* (2006.01)

(52) U.S. Cl.
CPC .... *A61M 25/0606* (2013.01); *A61M 25/0693* (2013.01); *A61M 25/09041* (2013.01); *A61M 2025/09116* (2013.01)

(58) Field of Classification Search
CPC .......... A61M 25/0606; A61M 25/0693; A61M 25/09041; A61M 25/065; A61M 2025/09116
See application file for complete search history.

(56) References Cited

U.S. PATENT DOCUMENTS

| | | | | |
|---|---|---|---|---|
| 4,894,052 A | * | 1/1990 | Crawford | A61M 25/0693 604/507 |
| 5,318,541 A | * | 6/1994 | Viera | A61M 25/09041 604/159 |
| 5,346,498 A | * | 9/1994 | Greelis | A61M 25/0119 606/108 |
| 6,217,558 B1 | * | 4/2001 | Zadini | A61B 5/150244 604/164.01 |

(Continued)

FOREIGN PATENT DOCUMENTS

DE    102006001255 A1 * 7/2007  ........ A61M 25/0075

*Primary Examiner* — Jason E Flick
*Assistant Examiner* — Adam J. Cermak
(74) *Attorney, Agent, or Firm* — Polsinelli PC

(57) ABSTRACT

An intravenous catheter system including a housing, a catheter, and a guide wheel rotatably disposed in the housing and manually engageable by the user. The intravenous catheter system may also include a guidewire contained within the housing and moveable by the guide wheel into and through the catheter with roation of the guide wheel with one finger, and push off tab. The intravenous catheter system may be configured such that once the guidewire is in a vein of a body, the user may use the same finger to advance the catheter by use of the push off tab A blood flash chamber can be incorporated into the housing of the system, method or device to indicate engagement between the catheter and the vein of the patient, and indicate the timing of the use of the wheel to move the guidewire.

19 Claims, 7 Drawing Sheets

(56) References Cited

U.S. PATENT DOCUMENTS

| | | | | |
|---|---|---|---|---|
| 6,626,869 | B1* | 9/2003 | Bint | A61M 25/09041 |
| | | | | 604/164.01 |
| 7,976,574 | B2* | 7/2011 | Papp | A61F 2/95 |
| | | | | 623/1.11 |
| 9,162,037 | B2 | 10/2015 | Belson et al. | |
| 10,143,826 | B2 | 12/2018 | Castro et al. | |
| 2004/0215146 | A1* | 10/2004 | Lampropoulos | A61B 5/15003 |
| | | | | 604/168.01 |
| 2005/0245847 | A1* | 11/2005 | Schaeffer | A61M 25/09041 |
| | | | | 600/585 |
| 2008/0300574 | A1* | 12/2008 | Belson | A61M 25/0606 |
| | | | | 604/510 |
| 2008/0319387 | A1* | 12/2008 | Amisar | A61M 25/0606 |
| | | | | 604/533 |
| 2010/0094310 | A1* | 4/2010 | Warring | A61M 25/0631 |
| | | | | 606/108 |
| 2010/0241177 | A1* | 9/2010 | Schaller | A61F 2/4611 |
| | | | | 606/86 A |
| 2011/0071502 | A1* | 3/2011 | Asai | A61M 25/0606 |
| | | | | 604/528 |
| 2011/0288533 | A1* | 11/2011 | Koch | A61M 25/09 |
| | | | | 604/528 |
| 2012/0197200 | A1* | 8/2012 | Belson | A61M 25/06 |
| | | | | 604/164.12 |
| 2012/0283640 | A1* | 11/2012 | Anderson | A61M 25/09 |
| | | | | 604/164.1 |
| 2015/0202414 | A1* | 7/2015 | Hwang | A61B 5/150389 |
| | | | | 600/585 |
| 2016/0121086 | A1* | 5/2016 | Castro | A61M 25/0113 |
| | | | | 600/585 |
| 2016/0256667 | A1* | 9/2016 | Ribelin | A61M 25/09041 |
| 2017/0296792 | A1* | 10/2017 | Ornelas Vargas | A61B 17/3468 |
| 2018/0126126 | A1* | 5/2018 | Ornelas Vargas | A61B 17/3468 |
| 2020/0001050 | A1* | 1/2020 | Garrison | A61M 25/0612 |
| 2020/0147349 | A1* | 5/2020 | Holt | A61M 25/0693 |
| 2020/0197682 | A1* | 6/2020 | Franklin | A61M 25/0097 |
| 2022/0080159 | A1* | 3/2022 | Garrison | A61M 25/0631 |

* cited by examiner

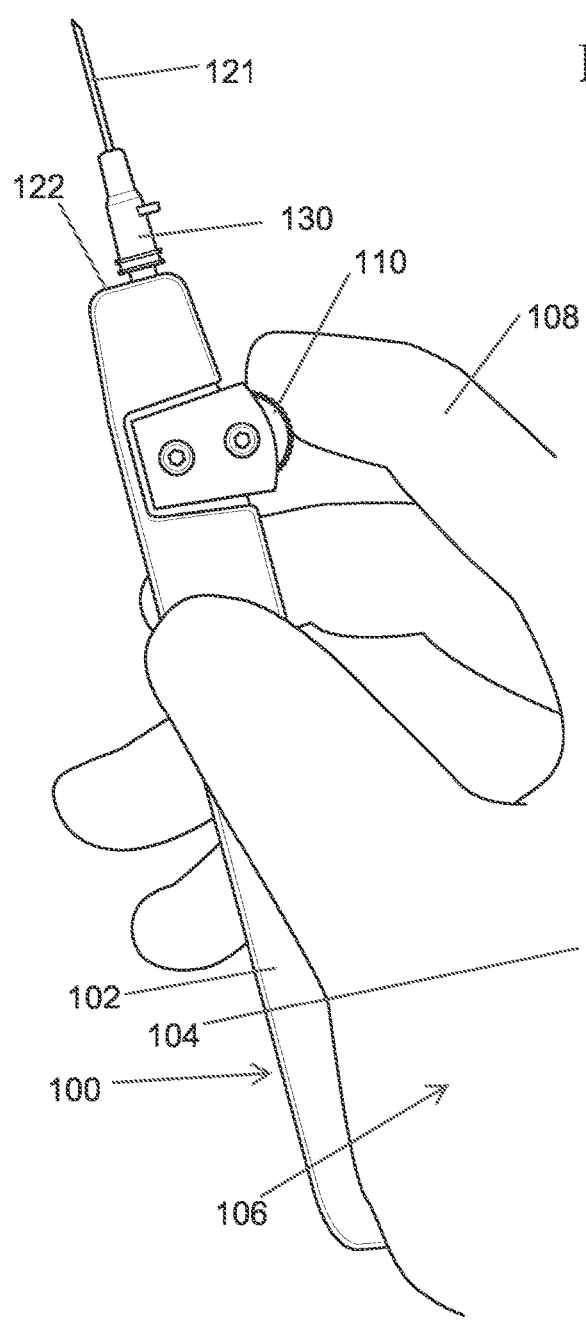
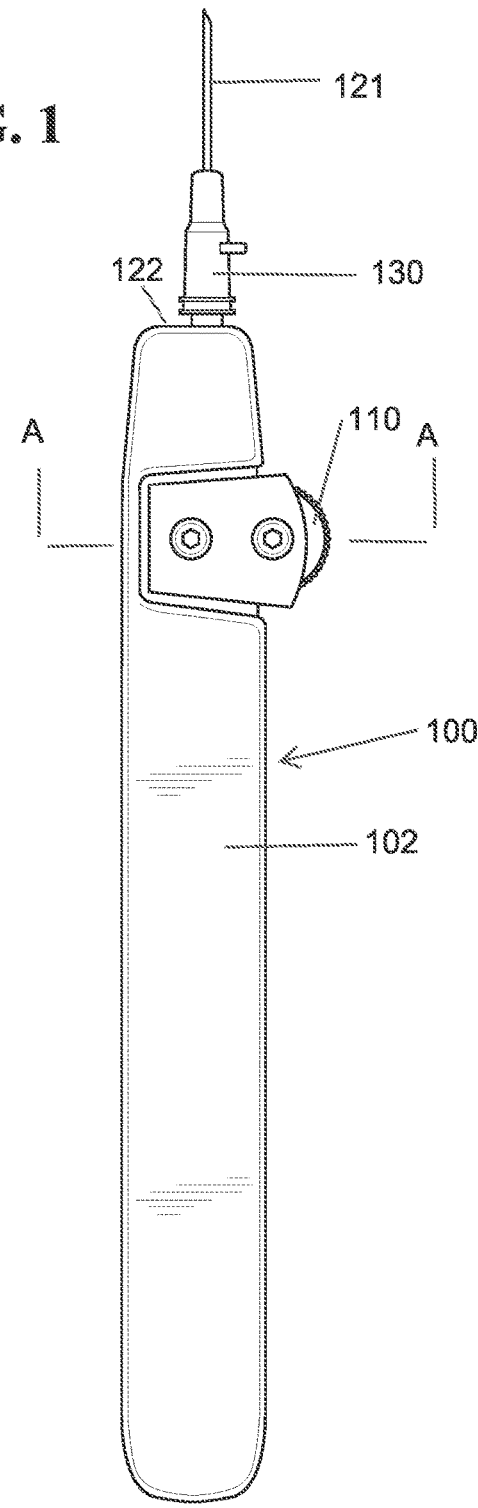
FIG. 1
FIG. 2

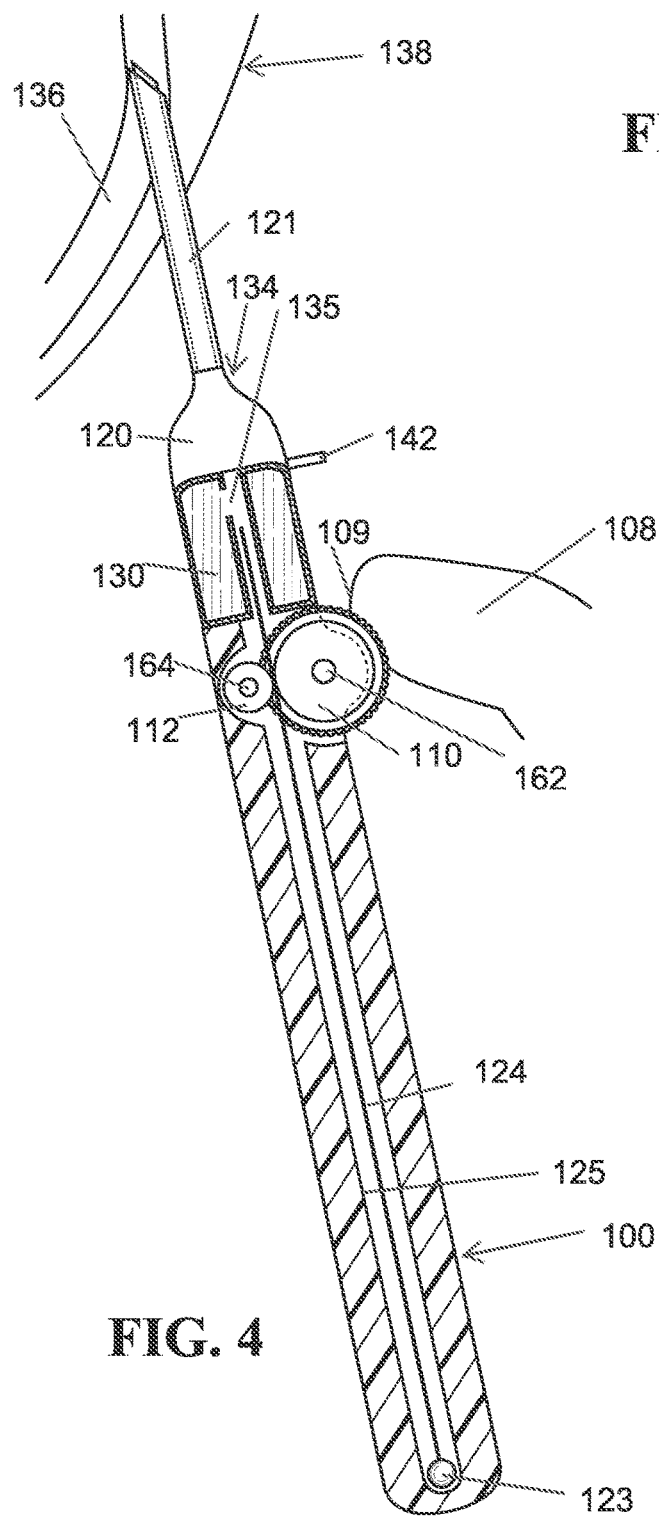
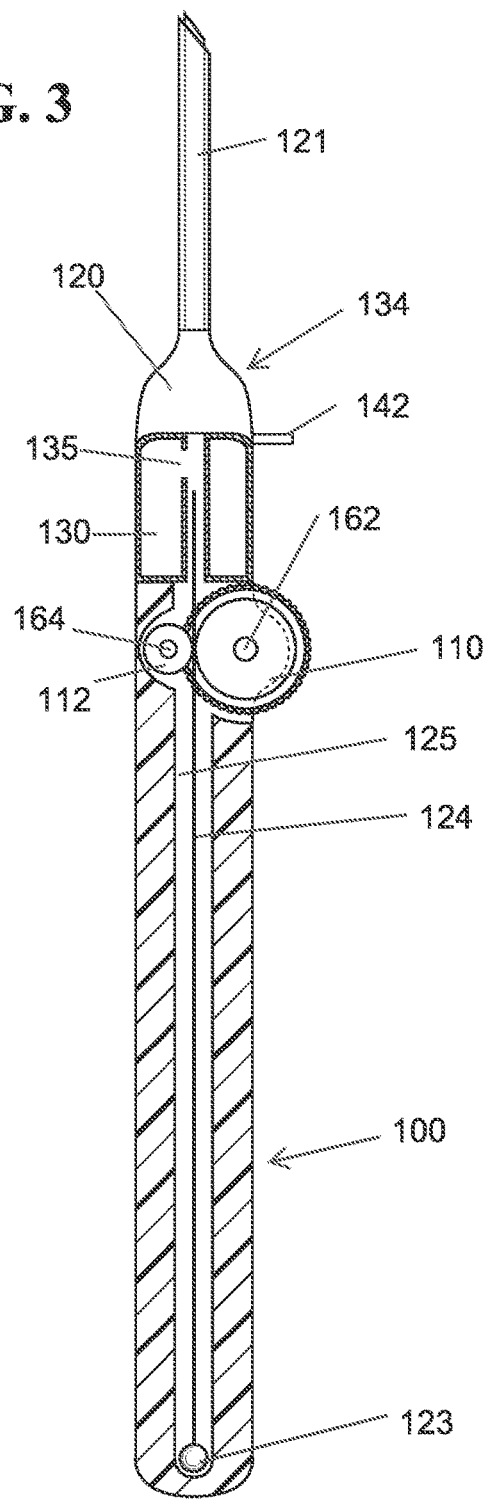

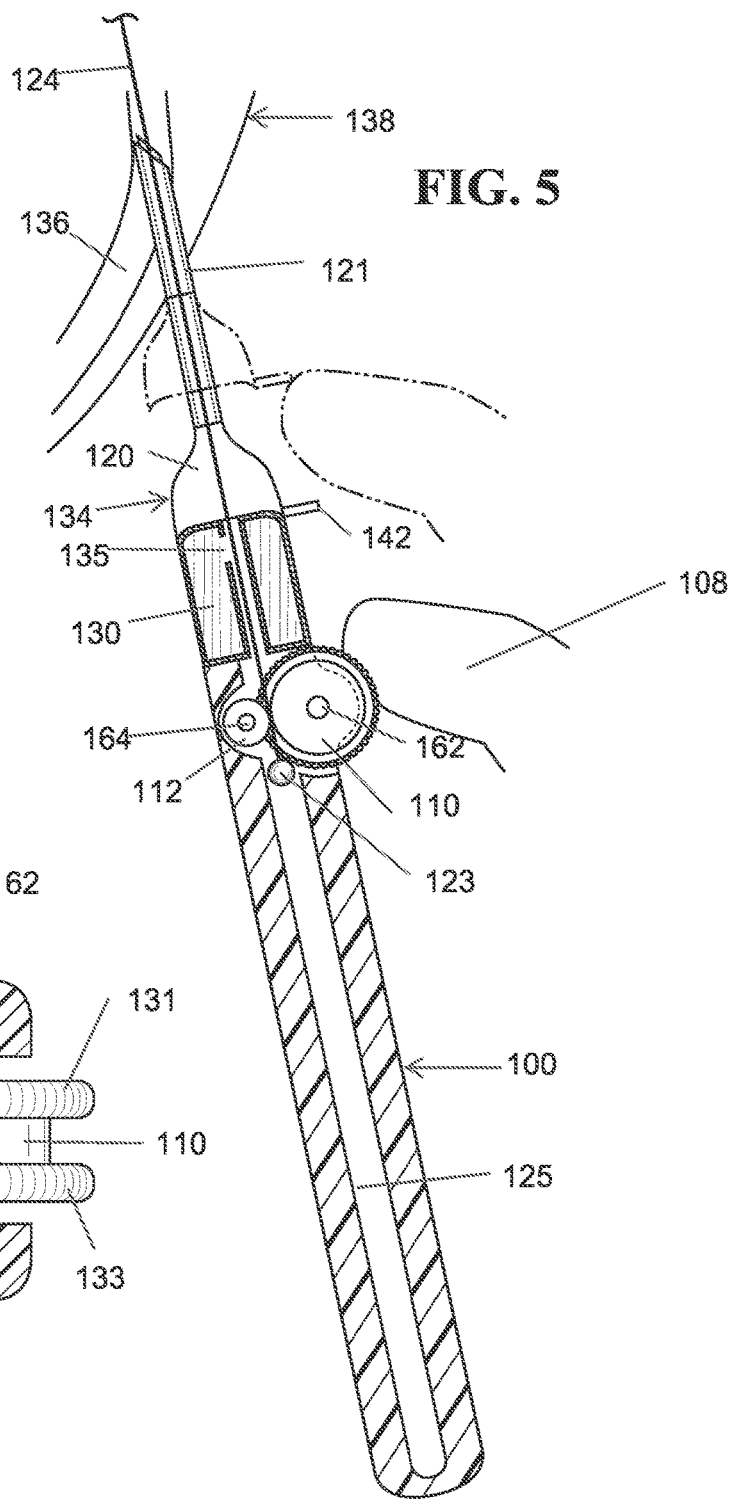

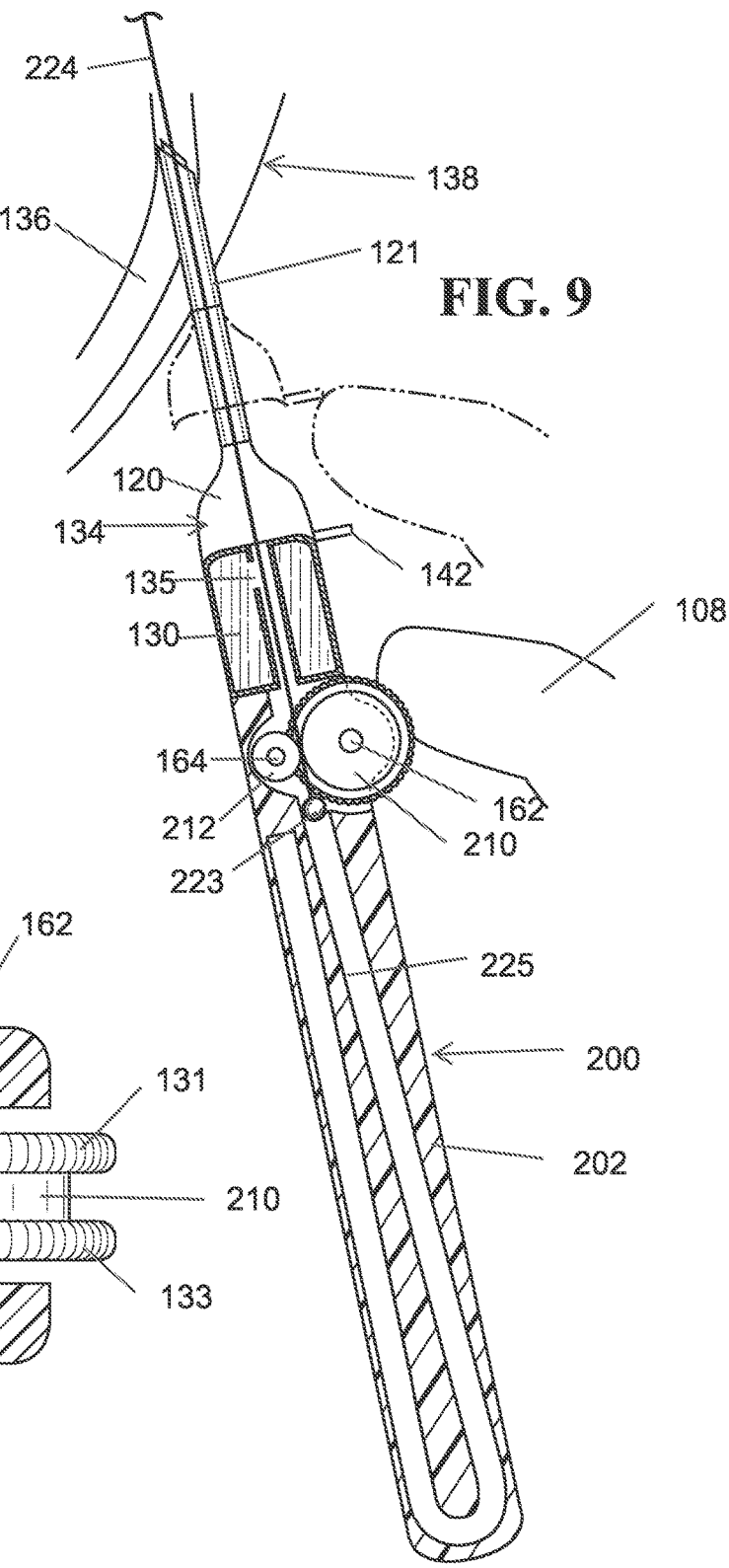

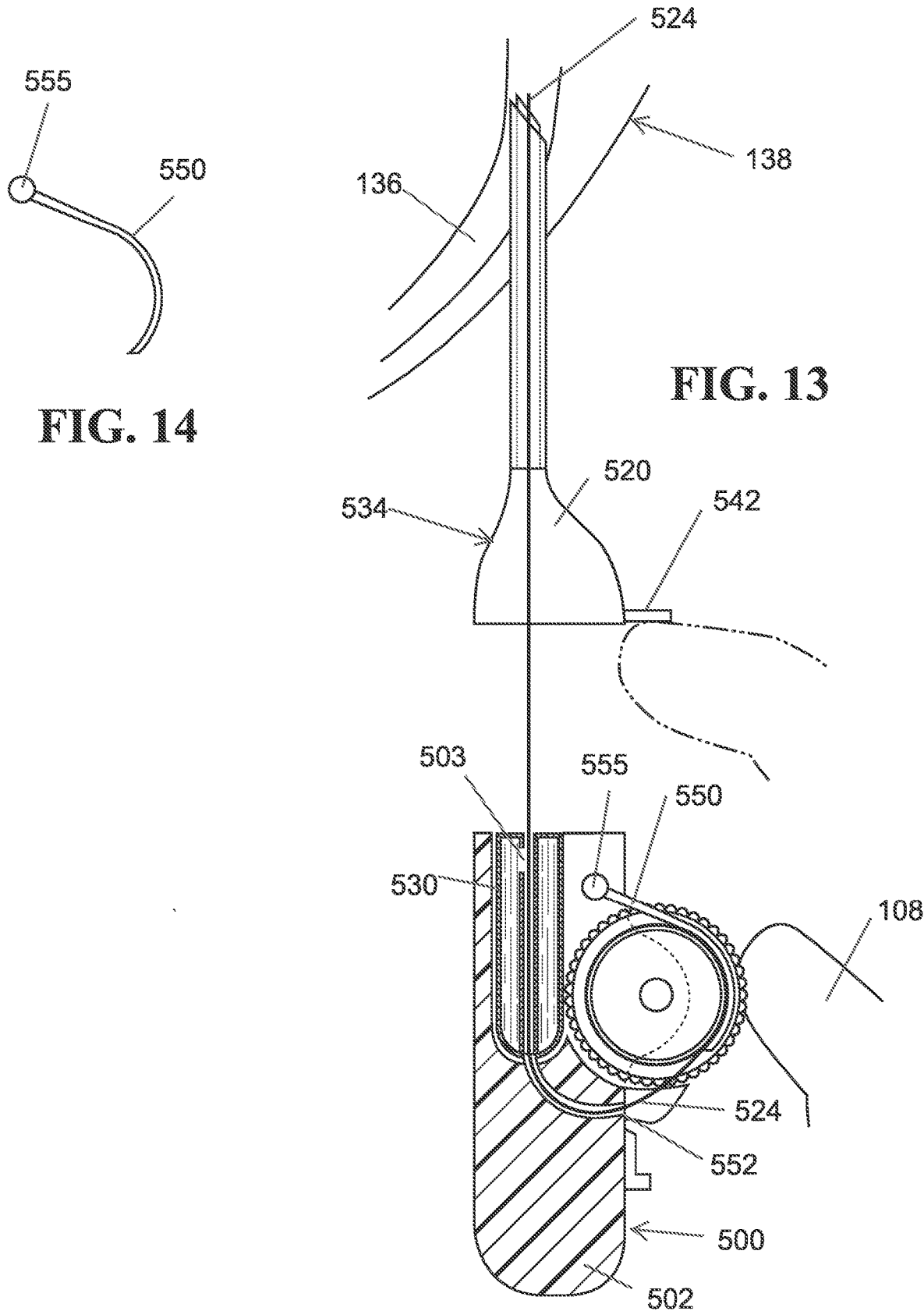

INTRAVENOUS CATHETER AND GUIDEWIRE ADVANCEMENT MECHANISM

RELATED APPLICATIONS

This application claims priority to and the benefit of U.S. Provisional Patent Application No. 62/923,494 filed Oct. 19, 2019, U.S. Provisional Patent Application No. 62/936,516 filed Nov. 17, 2019, U.S. Provisional Patent Application No. 62/937,971 filed Nov. 20, 2019, U.S. Provisional Patent Application No. 62/947,201 filed Dec. 12, 2019, and U.S. Provisional Patent Application No. 63/034,312, filed Jun. 3, 2020, the entire contents of which are hereby incorporated by reference.

FIELD OF THE INVENTION

This invention is an improvement to current guidewire assisted intravenous catheter's by using a built-in front wheel that allows for easy one-handed advancement of both a guidewire and plastic catheter with or without ultrasound imaging. This invention also allows for a familiar blood flash chamber similar to previous (non-guidewire) intravenous (IV) catheters that is missing with current guidewire IV catheter systems.

BACKGROUND AND SUMMARY

Most IV catheters used today in the United States lack guidewires for IV catheter placement. A problem with the older style IV catheters is that it's possible to get a blood flash, indicating that the needle is in the vein lumen, however the plastic catheter that is over the needle is still outside the vein. This is because there is an offset between the tip of the needle and the start of the plastic catheter that is over the needle. This can lead to inappropriate placement of the catheters and failed IV attempts once the operator tries to advance the plastic catheter when it is partially or completely outside the vein. A potential way to prevent this from happening is using a guidewire that goes through the needle and then advancing the plastic catheter over the guidewire (Seldinger technique).

An issue with the current guidewire assisted intravenous catheters on the market today is a lack of a familiar hand position for advancing the guidewire and catheter with one finger. Many operators who place non-guidewire intravenous catheters do so in a usual fashion of having their thumb and middle finger on each side of the needle grip and their index finger on top of the catheter near a push off tab. Up until now, there is no IV catheter on the market with a built-in all-inclusive IV catheter system that allows for an obvious blood flash similar to previous IV catheters, and a front wheel that allows for similar one handed biomechanics for advancing both a guidewire and catheter with the same finger. There is an introducer device on the market that utilizes a front wheel to direct a guidewire, U.S. Pat. No. 10,143,826 B2, however this is an introducer device only that needs to adjoin to another IV catheter and not an all in one IV catheter device. Also, this device prevents a blood flash from being visible with many of the IV catheters available on the market, limiting its function to mainly being utilized with ultrasound. Up until now there is no built-in all-in-one IV catheter with a front wheel guidewire system that helps achieve similar biomechanics to previous non-guidewire IV catheters that also allows for a familiar blood flash. The current all-in-one guidewire IV catheter on the market (AccuCath®) has a slide for advancing the guidewire through the needle that cannot be done with one hand alone. This IV catheter also has a difficult to see blood flash contained within the plastic catheter portion and lacks the more familiar blood flash chamber. With the vast advancement of ultrasound in the last decade, it is important to be able to get an obvious blood flash and then advance an IV guidewire/catheter system with one hand alone so the operator's other hand can simultaneously operate an ultrasound probe. The AccuCath® IV catheter lacks this capability as the ultrasound probe needs to be put down so the operator can advance the guidewire and catheter with their free hand.

Up until now, guidewire assisted intravenous catheters have lacked a blood flash similar to catheters without guidewires. Having a guidewire already in the needle can interfere with blood return ultimately leading to a less obvious flash of blood when the needle enters the vein. The problem with the introducer with U.S. Pat. No. 10,143,826 B2, is that the device has to connect directly to the needle blood return system so that the guidewire can advance through the needle, however this prevents a blood flash. This would make using this introducer device impractical if not impossible without an ultrasound machine. The AccuCath® has a difficult to see blood flash within the catheter itself and lacks a traditional blood flash chamber to alert the operator that the needle has entered the vein. An obvious blood flash is important for operators to know that they are in the vein lumen prior to advancing the guidewire, especially without ultrasound guidance.

Often an operator will hold the catheter with their middle finger and thumb on each side of the needle grip and their index finger free to move to advance a plastic catheter with the help of a push off tab once they think the plastic catheter is inside the vein. The solution of the present invention to the biomechanics problem of previous guidewire IV catheters is a built-in front wheel with a guidewire inside of it that can be advanced easily with one finger (usually the index finger, but variations are allowed based on preference). Once the guidewire is in the vein, the user can then use his/her same finger to advance the plastic catheter by use of a push off tab. Currently there is no built-in all-in-one IV catheter system that has a front wheel in the usual grip position that allows for guidewire advancement when doing IV catheters.

One embodiment of the present invention has a front wheel with a guidewire contained inside it and an inner frame that allows for guidance of a guidewire to go into a small hole located on the top of the needle. As the guidewire is advanced by rotating the front wheel, the guidewire will ultimately go through the needle and into the vein. Because the guidewire does not originate inside the needle, and nothing connects to the blood return system, it does not interfere with blood return into the flash chamber and a familiar flash should be obtained. Once the blood flash is obtained, the operator can turn the front wheel, advancing the guidewire first through the hole at the top of the needle, and then into the vein. Once the guidewire is fully inserted the operator can use the push off tab with the same finger to slide the plastic catheter over the guidewire and into the vein lumen.

The all-inclusive IV catheter of the present invention contains a built-in front wheel for one handed guidewire advancement to help provide proper biomechanics for IV catheter insertion. This design will allow for the complete process to be finished with one hand alone and the design will allow for an obvious blood flash so that it can be used easily with or without an ultrasound machine. The one-handed technique frees up the user's other hand so that the user can use ultrasound assistance while simultaneously visualizing the guidewire and catheter going into the vein. All of this can be performed without putting the ultrasound probe down and allowing for similar biomechanics used with previous non-guidewire intravenous catheters.

Current guidewire intravenous catheters lack a built-in, all-inclusive front wheel that allows ideal advancement of a guidewire into the vein lumen. The plastic catheter can then be inserted over the guidewire with the same finger with the help of a push off tab. Current guidewire IV catheter systems available today lose the obvious blood flashes of non-guidewire IV catheters and some systems have no blood flash at all. The design of the present invention allows for a similar blood flash to non-guidewire IV catheters, since the guidewire is not inside the needle prior to going into the vein and not an introducer device that connects directly to the blood return system of an entirely separate IV catheter. This device helps keep similar operator biomechanics that have been used with previous non-guidewire IV catheters. The present invention allows for complete one-handed advancement of a guidewire and plastic catheter without changing hand position so that the other hand can utilize ultrasound for the entire procedure without having to put the ultrasound probe down to advance the guidewire and catheter.

BRIEF DESCRIPTION OF THE DRAWINGS

Advantages of the present invention will be readily appreciated as the same becomes better understood by reference to the following detailed description when considered in connection with the accompanying drawings wherein:

FIG. 1 is an elevated perspective view of an intravenous catheter product;

FIG. 2 is an elevated perspective view of the product of FIG. 1 set in the hand of a user of the product;

FIG. 3 is a vertical sectional view of the product of FIG. 1;

FIG. 4 is a vertical sectional view of the product of FIG. 1 associated with a patient shown in elevation;

FIG. 5 is a vertical sectional view similar to FIG. 4 with the patient in elevation and the guide wire of the product disposed further into the patient;

FIG. 6 is a vertical section view along the lines A-A of FIG. 1 with the two wheels portions and two axle portions in elevation;

FIG. 9 is a view similar to FIG. 8 with the guide wire disposed further into the patient;

FIG. 10 is a vertical sectional view similar to FIG. 6 of the embodiment of FIGS. 7, 8 and 9;

FIG. 13 is a vertical section view of the alternative of FIG. 11 including an illustration of the patient in section and the finger of the user in elevation and in a second position in phantom, as well as a portion of the product in elevation; and FIG. 14 illustrates the tensioner and securement element.

DETAILED DESCRIPTION

Figure 8:
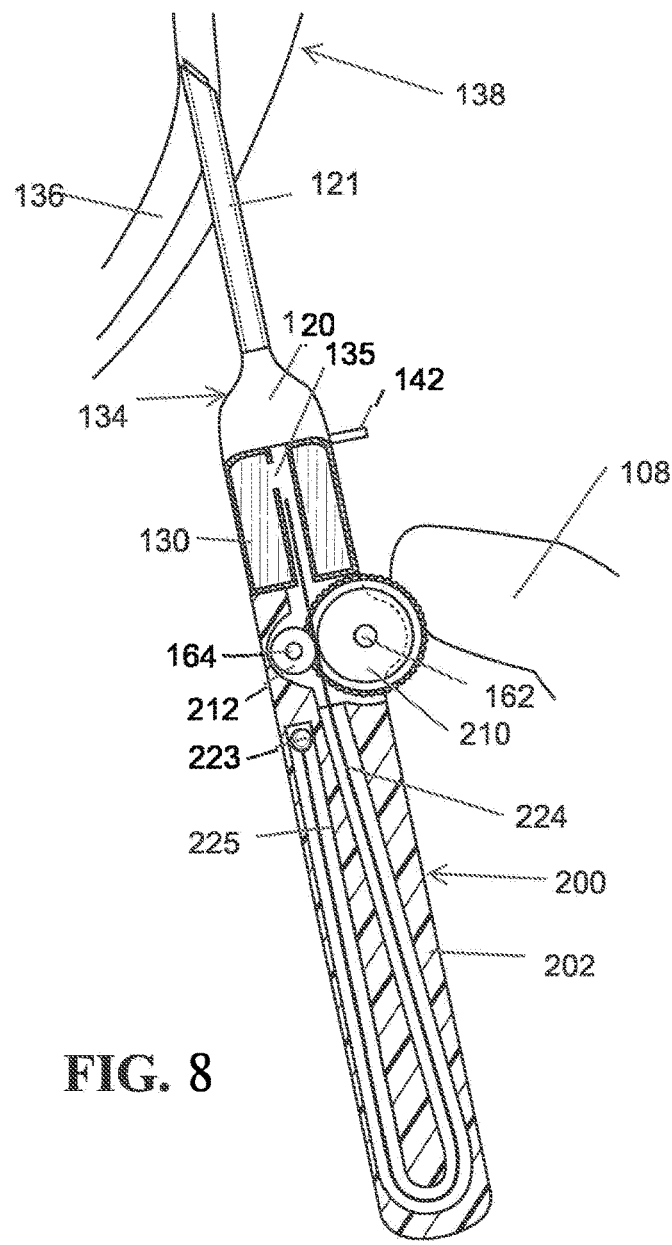
FIG. 8 is a vertical sectional view similar to FIG. 7 with the patient shown in section and a finger of the user shown in elevation.
Figure 7:
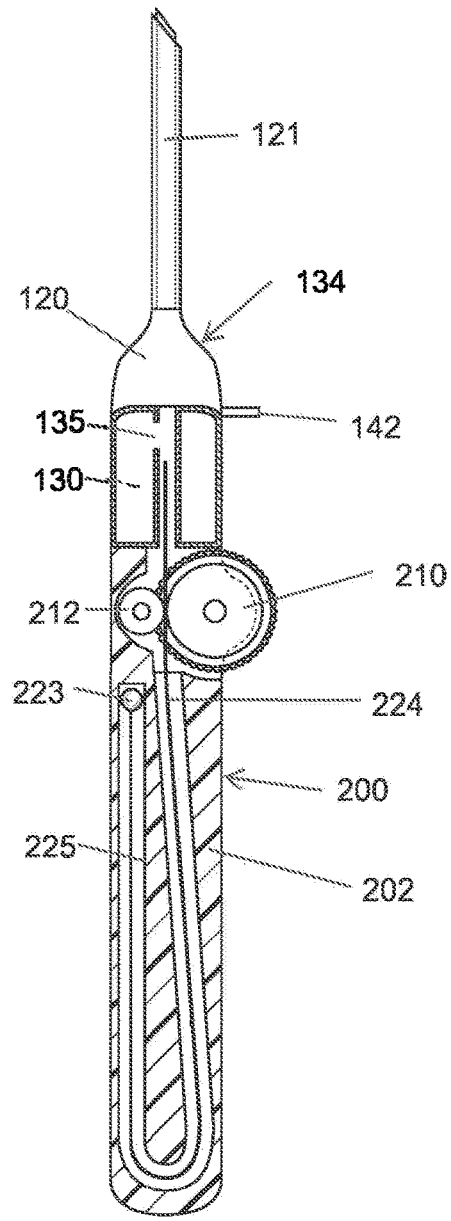
FIG. 7 is a vertical sectional view of an alternative version of the product of the present invention.
Figure 12:
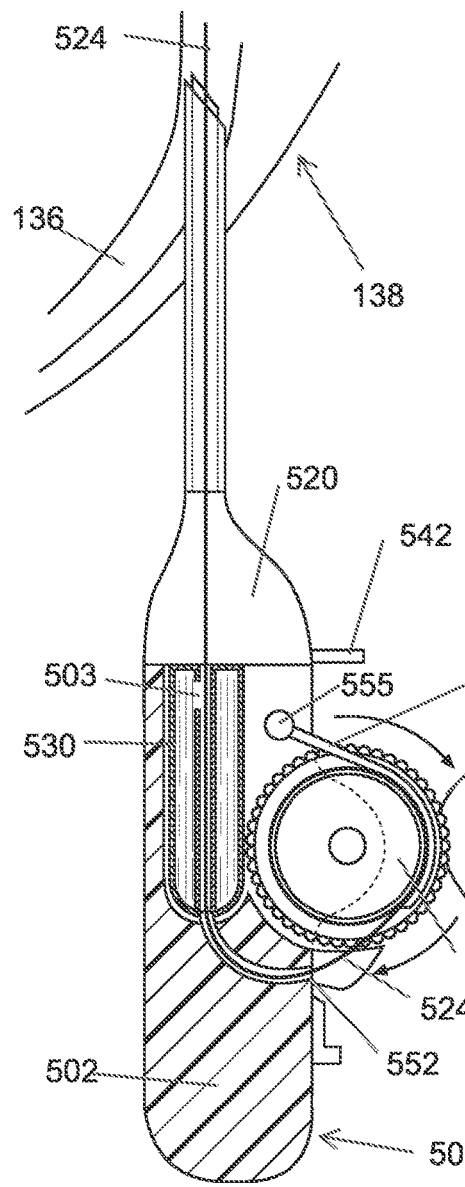
FIG. 12 is a view similar to FIGS. 3 and 7 of the alternative of FIG. 11 with the patient in section and the finger of the user in elevation along with a portion of the product in elevation.

FIG. 1 illustrates the general appearance of the intravenous catheter guidewire system or product 100 in a handheld outer housing 102 usually made in two pieces. As shown in FIG. 2, the system 100 can be used with one hand 104 by an operator 106 placing one finger 108 on a guide wheel 110 to operate the guide wheel 110. A catheter 120 is attached to the forward end 122 of the housing 102 in a conventional detachable manner.

FIG. 3 illustrates the general appearance of the intravenous catheter guidewire system or product 100, primarily in section, with a guidewire 124 built to interact functionally with the guide wheel 110. A traditional blood flash chamber 130 clear and visible to the operator 106 for a needle 134 is shown that should fill with an obvious blood flash through a hole 135 once the vein 136 is engaged (FIG. 4) since there is no guidewire obstructing blood flow into the chamber 130. Note that the chamber 130 is enlarged in this view relative to the housing 102, but the size of the chamber 130 can vary, while the blood flash function can be representative regardless of the scale to the housing as a flash of blood. A catheter 120 is included as part of the needle 134 and is detachable.

The guidewire 124 is originally disposed in the needle 134 above the needle hole 135 located at the top of the chamber 130. Blood return occurs (FIG. 4) at the needle hole 135 and should cause a blood flash visible to the operator 106 once the needle 134 is inside the vein 136 of a patient 138 (guidewire 124 blocks blood return out of the end of the needle 134 forcing the blood to enter the needle hole 135). This is also a signal to operate the guidewire 124. A push off tab 142 is connected to the catheter 120 and assists with pushing the catheter 120 into the vein 136 with one finger 108 after the guidewire 124 has been advanced, as well as detaching the catheter 120 as shown in FIG. 5.

FIG. 4 illustrates rotating the guide wheel 110 in a backwards direction with the pad 109 of a finger 108 causes the guidewire 124 via friction with the guide wheel 110 and a support wheel 112 to go into the needle 134 and ultimately into a vein 136. An inner track 125 directs the guidewire 124 into the needle 134 as moved between the guide wheel 110 and support wheel 112. Operating guide wheel 110 as in this manner, the inner track 125 should also cause the guidewire 124 to only advance toward the tip of the needle 134 because of the shape of the inner track 125 and a ball element 123 disposed on the trailing end of the guidewire 124 that centers the guidewire in the track 125 and also stops the guidewire 124 from proceeding beyond the guide wheel 110 and support wheel 112. Traditional grip locations 131, 133, as illustrated in FIG. 6, are on each side of the guide wheel 110 to move the guide wheel 110. The traditional grip locations may also refer to placement of the thumb and middle finger on opposed sides of the housing, as illustrated in FIG. 2.

FIG. 5 illustrates once the blood flash is obtained, the guidewire 124 is fully advanced with the pad 109 of a finger 108 until the guide wheel 110 stops. Then the operator uses the same finger 108 that turned the guide wheel 110 to push on the push off tab 142 to advance the catheter 120 over the guidewire 124 and into the vein 136.

FIG. 6 illustrates the guide wheel 110 that contains the guidewire 124 between the guide wheel 110 and the support wheel 112, which are each mounted to rotate on axles 162 and 164 respectively and are disposed to frictionally engage the guidewire 124 to move the guidewire 124 forwardly or backwardly in response to movement of the guide wheel 110 by the finger 108 of the operator 106. The part of the guide wheel 110 that has contact with the guidewire 124 will be covered with a plastic or rubber type of material (e.g., thermoplastic polyurethane but not limited to this material) that allows the guidewire 124 to be gripped by the guide wheel 110 and prevent slippage of the guidewire 124. The support wheel 112 would preferably have a similar covering.

The guidewire 124 is contained within the IV catheter 120 covered by a frame 121 of the IV catheter in a sterile fashion. The guidewire 124 will be made of a material such as nitinol or other similar alloy metals that may allow for frictional contact with the guide wheel 110 and support wheel 112 and then be able to be guided through the needle 134 and into the vein 136. The guidewire 124 will advance past the needle hole 135 and should go towards the tip of the needle 134 because of the shape of the inner frame.

FIGS. 7 to 10 illustrate an alternative embodiment of the system or product 200 where the guidewire 224 is provided a longer length of travel in a shorter length of housing 202 in the same general outer configuration but shorter in length. The guide wheel 210 and support wheel 212 can be the same or very similar configuration as the prior embodiment described above, but an extended track 225 is included that would add a distance of travel for the guidewire within the housing 202, and would loop within the housing 202 as shown. A stop ball 223 is disposed at the end of the guidewire 224 within the track to center the guidewire 224 on the track 225 and also stop the guidewire 224 once the stop ball 223 reaches the guide wheel 210 and support wheel 212. Similar to the prior versions, the guidewire 224 moves between the guide wheel 210 and the support wheel 212 which are each mounted to rotate on axles 162 and 164 respectively and disposed to frictionally engage the guidewire 224 to move the guidewire 224 forwardly or backwardly in response to movement of the guide wheel 210 by the finger 108 of the operator 106. In all other respects, this embodiment would function in the same manner as that of FIGS. 2 through 6. The guidewire 224 movement would occur after the blood flash appears in the chamber 130 after engagement of the vein 136 (FIG. 8) and subsequent blood flow into the chamber 130 (FIG. 9) before movement of the guidewire 224.

Figure 11:
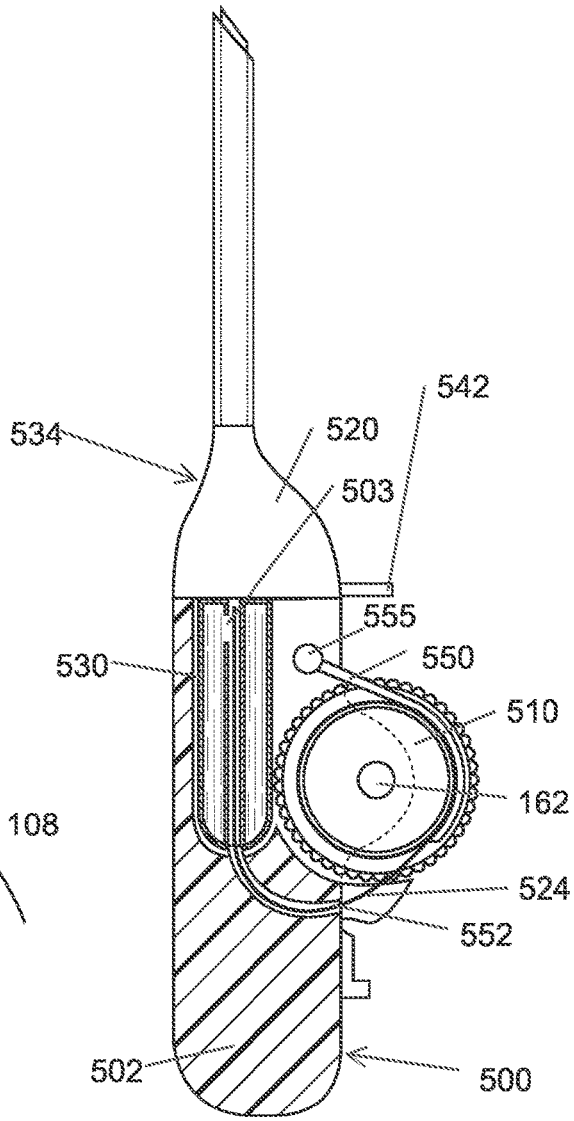
FIG. 11 is a vertical sectional view of a further alternative view of the present invention with portions in elevation.

FIGS. 11 through 14 disclose a further embodiment of the invention having a shorter length housing 502 and a guide wheel 510 in which the guidewire 524 wraps around the guide wheel 510 as it is manipulated by the finger 108 of an operator 106. FIG. 13 illustrates the general appearance of the intravenous catheter guidewire system or product 500 with a guidewire 524 built into the guide wheel 510 to wrap around the guide wheel 510. The blood flash chamber 530 is shown as a clear plastic portion of the housing 502 that is visible to an operator 106 and that should fill with an obvious blood flash since there is no guidewire obstructing blood flow into the chamber 530 via a hole 503. The guidewire 524 is originally disposed just inside the needle 534 above the needle hole 503 located in the needle 534 (FIG. 11). The guidewire 524 moves from the guide wheel 510 into a passageway 552 in the housing 502, through the blood flash chamber 530 into the needle 534. Blood return occurs at the needle hole 503 and should cause a blood flash once the catheter 520 is inside the vein 136 of a patient 138 (the guidewire 524 blocks return through the end of the needle 534). A push off tab 542 is connected to the catheter 520 and assists with pushing the catheter 520 into the vein 136 and disconnecting with the housing 502 with one finger 108 after the guidewire 524 has been advanced as shown in FIG. 13.

A spring loaded tensioner 550 is fixed to the housing at one end via a securement element 555 and wrapped around the guidewire 524 on the guide wheel 510 to control the radial position of the guidewire 524 on the guide wheel 510 as it is reeled in or out during movement of the guide wheel 510 and relative movement of the guidewire 524. The guidewire 524 is wrapped around the guide wheel 510 more than one time, generally, and is secured to the guide wheel 510 at the end opposite to the end entering the vein 136. This construction permits more linear travel of the guidewire 524 in a shorter length of housing 502 to obtain the same results as described above. The tensioner 550 is shown separately in FIG. 14 and would conventionally be made from a spring steel material, preferable stainless steel, with a securement element 555 either welded to the steel if a metal stop or molded to the steel if a plastic element. The guide wheel 510 may be larger in diameter than the guide wheels of the other embodiments to accommodate more travel for fewer turns of the guide wheel 510 as the guidewire 524 wraps around the guide wheel 510.

In this case the guidewire 524 will be covered by a plastic material (but not limited to plastic material) to help keep it sterile. This covering will protect the guidewire 524 from the operator's gloved finger 108.

It should also be noted that with slight modifications in needle length and types of plastic catheters, the invention can be used with central and arterial lines in the same manner as described above.

The instant disclosure has been described in an illustrative manner, and it is to be understood that the terminology which has been used is intended to be in the nature of words of description rather than of limitation. Obviously, many modifications and variations of the instant disclosure are possible in light of the above teachings. It is, therefore, to be understood that within the scope of the appended claims, the instant disclosure may be practiced otherwise than as specifically described.

The invention claimed is:

1. An intravenous catheter system comprising:
   a housing;
   a catheter attached to a forward end of the housing;
   a guidewire completely disposed within a track defined by the housing;
   a guide wheel disposed in the housing, the guide wheel comprising:
      an inner surface configured to engage the guidewire and move the guidewire; and
      an outer surface spaced from the inner surface, the outer surface contactable by a user to manipulate the guide wheel and move the guidewire;
   a ball element disposed on a trailing end of the guidewire that centers the guidewire in the track and also stops the guidewire from proceeding beyond the guide wheel;
   a passageway in the catheter extending from a first end for insertion into a patient to a second end associated with said housing; and
   a chamber into which blood flows from the patient through the catheter once a vein of a patient is engaged with the catheter.

2. The intravenous catheter system in accordance with claim 1, wherein the chamber is visible to the user to disclose a blood flash once a needle of the catheter enters the vein of a patient.

3. The intravenous catheter system in accordance with claim 1, further comprising said catheter having a push off tab, wherein once a needle and the guidewire enter the vein of a body, a user can then use a finger to advance the catheter into the vein by use of the push off tab.

4. The intravenous catheter system in accordance with claim 1, wherein said track forms a loop within said housing.

5. The intravenous catheter system in accordance with claim 1, wherein the chamber is disposed on the housing and is positioned distal to the guide wheel, the chamber defining a bore connected to the passageway and configured to receive the guidewire;
    an aperture providing fluid communication between the bore and a void defined by the chamber, the void for receiving blood once a needle of the catheter enters the vein of a patient;
    wherein a distal end of the guidewire is movable with the guide wheel between:
        a first position where the distal end of the guidewire is proximal to the aperture in the bore such that the guidewire will not obstruct the flow of blood into the void through the aperture; and
        a second position where the distal end of the guidewire is distal to the aperture in the bore after a blood flash has been achieved.

6. The intravenous catheter system of claim 1, wherein the housing forms the track that extends from the guide wheel to an end of the housing.

7. The intravenous catheter system of claim 6, wherein the ball is operable to traverse the track from a start of the track until the ball contacts with the guide wheel.

8. A method for using an IV catheter with a guidewire, the method comprising:
    contacting an outer surface of a guide wheel with an index finger of a user, the inner surface configured to engage the guidewire;
    rotating the guide wheel through the contact by the user with the outer surface to insert the guidewire into a vein of a patient;
    centering the guidewire within a track defined by a housing by having a ball element disposed on a trailing end of the guidewire traverse the track;
    stopping, when the ball element contacts the guide wheel, the guidewire from proceeding beyond the guide wheel; and
    manipulating a push off tab with the index finger to advance the catheter once the guidewire is in a vein of a patient.

9. An IV catheter used by a medical professional, comprising:
    a housing;
    a catheter;
    an integral guide wheel rotatably disposed in said housing, the guide wheel comprising an outer surface that is manually engageable by the medical professional and an inner surface that is spaced from the outer surface;
    a guidewire contained within a track defined by the housing and in contact with the inner surface of the guide wheel, the guidewire moveable by rotation of the inner surface of said guide wheel into and through said catheter;
    a ball element disposed on a trailing end of the guidewire that centers the guidewire in the track and also stops the guidewire from proceeding beyond the guide wheel; and
    a push off tab disposed on the catheter, wherein once the guidewire is in a vein of a body, the medical professional can then use the push off tab to advance the catheter into the vein of the patient.

10. The IV catheter in accordance with claim 9, further comprising a grip disposed on the outer surface of said guide wheel to assist the medical professional with rotation of the guide wheel.

11. The IV catheter in accordance with claim 9, further comprising a second rotatable element adjacent said guidewire to engage said guidewire to move said guidewire.

12. The IV catheter in accordance with claim 11, wherein said guide wheel and said second rotatable element are disposed on opposed sides of the guidewire and work together to move said guidewire in a manner controlled by said medical professional.

13. The IV catheter in accordance with claim 9, wherein said track forms a loop within said housing.

14. A catheter in accordance with claim 9, wherein said track forms a C-shape within said housing.

15. An intravenous catheter system comprising:
    a housing defining a track;
    a catheter;
    a guidewire;
    a guide wheel disposed in the housing to engage the guidewire and move the guidewire;
    a ball element disposed on a trailing end of the guidewire that centers the guidewire in the track and also stops the guidewire from proceeding beyond the guide wheel;
    a passageway in the catheter from one end used on a patient to a second end associated with said housing; and
    a chamber defining a bore in communication with the passageway, the bore configured to receive the guidewire;
    an aperture providing fluid communication between the bore and a void defined by the chamber, the void for receiving blood from the patient through the passageway of the catheter once a needle of the catheter enters a vein of the patient.

16. The system in accordance with claim 15 wherein the chamber is visible to the user to disclose a blood flash once the needle of the catheter enters the vein of a patient.

17. The system in accordance with claim 15, wherein said catheter has a push off tab, wherein once the needle of the catheter and the guidewire is in the vein of a body, the medical professional can then use the push off tab to advance the catheter into the vein of the patient.

18. The intravenous catheter system in accordance with claim 15, wherein said track forms a loop within said housing.

19. The intravenous catheter system in accordance with claim 15, wherein the chamber is disposed on the housing and is positioned distal to the guide wheel;
    wherein a distal end of the guidewire is movable with the guide wheel between:
        a first position where the distal end of the guidewire is proximal to the aperture in the bore such that the guidewire will not obstruct the flow of blood into the void through the aperture; and
        a second position where the distal end of the guidewire is distal to the aperture in the bore after a blood flash has been achieved.

\* \* \* \* \*